| United States Patent [19] | [11] 4,180,572 |
|---|---|
| Carr | [45] Dec. 25, 1979 |

[54] LIPOGENESIS CONTROL BY ESTERS OF BENZOXAZINECARBOXYLIC ACIDS

[75] Inventor: John B. Carr, Houston, Tex.

[73] Assignee: Shell Oil Company, Houston, Tex.

[21] Appl. No.: 937,031

[22] Filed: Aug. 25, 1978

Related U.S. Application Data

[63] Continuation-in-part of Ser. No. 791,758, Apr. 28, 1977, abandoned.

[51] Int. Cl.$^2$ .............................................. A61K 27/00
[52] U.S. Cl. ............................ 424/248.55; 424/248.5
[58] Field of Search ......................... 424/248.5, 248.55

[56] References Cited

U.S. PATENT DOCUMENTS

| 3,625,969 | 12/1971 | Rossi | 424/248.5 |
|---|---|---|---|
| 3,929,803 | 12/1975 | Holland | 424/248.5 |

OTHER PUBLICATIONS

Chem. Abst., 76-113146Q (1972).

*Primary Examiner*—Stanley J. Friedman

[57] ABSTRACT

Lipogenesis in mammals is inhibited by esters of 3,4-dihydro-2H-1,4-benzoxazine-2-carboxylic acids.

9 Claims, No Drawings

LIPOGENESIS CONTROL BY ESTERS OF BENZOXAZINECARBOXYLIC ACIDS

This application is a continuation-in-part of application Ser. No. 791,758, filed on Apr. 28, 1977, now abandoned.

DESCRIPTION OF THE INVENTION

It has been found that lipogenesis in mammals is inhibited by esters of 3,4-dihydro-2H-1,4-benzoxazine-2-carboxylic acids which can be described by the formula

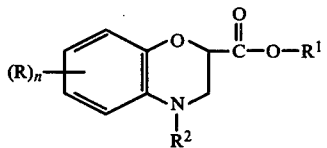

wherein n is zero, one or two, with the following provisos: (1) when n is one, R is middle halogen, nitro, amino, methylsulfonylamino, trifluoromethyl, phenyl, or alkyl or alkoxy of from one to six carbon atoms, bonded to a carbon atom in the 6-, 7-, or 8- position of the molecule; (2) when n is two, (a) R is nitro or middle halogen, bonded to carbon atoms in the 6- and 7- positions or is, (b) 6-nitro, 8-chloro; $R^1$ is alkyl of from one to four carbon atoms, and $R^2$ is hydrogen or phenalkyl. By middle halogen is meant bromine and chlorine, chlorine being preferred. Each alkyl moiety may be of straight-chain or branched-chain configuration. In the phenalkyl moiety, the "alkyl" portion may contain up to four carbon atoms, and preferably contains from one to two carbon atoms linking the phenyl moiety with the indicated ring nitrogen atom.

Preferred of these compounds, because of their activity in inhibiting lipogenesis, are those wherein n is zero, or n is one and R is nitro, methylsulfonylamino, or methoxy bonded to a carbon atom at the 6- or 7-position, $R^1$ is ethyl, and $R^2$ is hydrogen or benzyl.

Compounds of Formula I are basic in character and form salts with acids such as the hydrohalic acids, which are physiologically acceptable and also are effective inhibitors of lipogenesis in mammals. Such salts accordingly are included in this invention.

For illustration, preparation, preparation of typical individual species of the genus defined by Formula I are described in the examples included hereinafter. Other typical, illustrative individual species of the genus include those wherein the respective moieties are:

$R^1$ is ethyl, $R^2$ is hydrogen, n is one, R is:
6-bromo;
7-bromo;
8-bormo;
7-chloro;
$R^1$ is butyl, $R^2$ is hydrogen, n is zero.
$R^1$ is ethyl, $R^2$ is hydrogen, n is two, R is:
6-chloro,7-nitro;
6-nitro,7-bromo;
$R^2$ is hydrogen, n is zero, $R^1$ is:
methyl;
butyl.
$R^1$ is butyl, $R^2$ is benzyl, n is zero.
$R^1$ is butyl, $R^2$ is hydrogen, n is one, R is 6-nitro.
$R^1$ is propyl, $R^2$ is hydrogen, n is one, R is 6-methylsulfonylamino.
$R^1$ is ethyl, $R^2$ is benzyl, n is one, R is 6-nitro.

The ethyl ester of 3,4-dihydro-2H-1,4-benzoxazine-2-carboxylic acid is a known compound: British patent No. 1,057,568. Esters wherein the moiety, $R^1$, is other than ethyl can be prepared by the Fischer-Speier esterification of the acids, i.e., treating the corresponding acid with the appropriate alcohol, $R^1OH$, in a solvent such as toluene, in the presence of a catalytic amount of an acid such as sulfuric acid, hydrochloric acid, or para-toluenesulfonic acid. The precursor acids can be prepared by hydrolysis of the ethyl ester, using conventional techniques. Precursor esters wherein $R^2$ is alkyl can be prepared by condensing a methyl or ethyl ester of the appropriate 2,3-dibromobutyric, -pentanoic or -hexanoic acid with the appropriate 4-R-2-aminophenol, in the presence of a base such as potassium carbonate, in a solvent such as acetone, at or somewhat above room temperature. Some of the precursor phenols (R=H, chlorine, methyl, methoxy, nitro) are known. Methods for preparation of other phenols are shown in Examples 7 and 8 hereinafter, and by Katz et al., J. Org. Chem., 19 758 (1954).

Those species wherein R is methylsulfonylamino can be prepared by treating the species wherein R is amino with methanesulfonyl chloride in a solvent such as methylene chloride, in the presence of a base such as triethylamine or pyridine as shown in Example 6 hereinafter.

The procedures for preparing compounds of Formula I are illustrated in the following examples. In each case, the identities of the the product, and of the precursor(s) involved, were confirmed by appropriate chemical and spectral analyses.

EXAMPLE 1

Ethyl 3,4-dihydro-4-benzyl-2H-1,4-benzoxazine-2-carboxylate (1)

3,4-dihydro-2H-1,4-benzoxazine-2-carboxylic acid ethyl ester hydrochloride (1A) was prepared as white crystals, m.p.: 186°–188° (British patent 1,057,528: m.p.: 181°–185°) by the potassium carbonate mediated condensation of o-aminophenol and ethyl 2,3-dibromopropionate in dry acetone, according to the procedure shown in British patent No. 1,057,528.

1A was treated with sodium bicarbonate to prepare the free base (1B). A mixture of 5.3 g of 1B and 8.23 g of thallium ethoxide in 50 ml of dimethylformide was stirred at room temperature for 16 hours. 5.64 g of benzyl bromide then was added and the resulting mixture was stirred at room temperature for 5 hours. Thallium bromide precipitated and was filtered. The filtrate was stripped of solvent under reduced pressure and the residue was dry column chromatographed through silica gel using a 4:16:80 by volume mixture of tetrahydrofuran, ethyl acetate and hexane as eluent. The product was recrystallized from ether/hexane to give 1, as a solid, m.p.: 83.5°–84.5°.

EXAMPLE 2

Ethyl 6-chloro-3,4-dihydro-2H-1,4-benzoxazine-2-carboxylate (2)

43.0 g of 2-amino-4-chlorophenol was dissolved in 500 ml of anhydrous acetone containing 42.0 g of anhydrous potassium carbonate. That mixture was heated to reflux temperature and 23.0 g of ethyl 2,3-dibromopropionate was added slowly. In three additional portions each, additional ester and carbonate were added to the refluxing mixture until a total of 124 g of carbonate and 85.8 g of ester had been added. The mixture was refluxed for 21 hours. Solids were filtered from the mixture and the filtrate was stripped of solvent. The residue was taken up in water and the solution was extracted with ether. The ether extract was dried (MgSO$_4$) and the solvent was stripped. The residue was recrystallized from ethanol, eluted through a silica gel column using a 4:30:66 by volume mixture of tetrahydrofuran, ethyl acetate and hexane as eluent, and the product was recrystallized from ethanol, and then from ether, to give 2 as white crystals, m.p.: 85.5°–86.5°.

EXAMPLE 3

Ethyl 6-methyl-3,4-dihydro-2H-1,4-benzoxazine-2-carboxylate hydrochloride (3)

29.3 g of ethyl 2,3-dibromopropionate was added over a ten minute period to a refluxing mixture of 19.0 g of anhydrous potassium carbonate, 56.6 g of 2-amino-p-cresol and 500 ml of dry acetone. The procedure was repeated thrice as in Example 2. The mixture then was refluxed for 17 hours and filtered, and the filtrate stripped of solvent under reduced pressure. The liquid residue was diluted with 300 ml of 1 N sodium hydroxide solution at 5°–10° C., then extracted four times with 300 ml portions of ether. The extracts were combined, dried (MgSO$_4$) and treated with hydrogen chloride gas at 5°–10° C. A solid which formed was filtered and washed with acetone. The residue was recrystallized from ethanol to give 3, as white crystals, m.p.: 158°–160° C.

EXAMPLE 4 ethyl 6-nitro-3,4-dihydro-2H-1,4-benzoxazine-2-carboxylate (4)

29.2 g of ethyl 2,3-dibromopropionate was added dropwise to a refluxing mixture of 19 g of anhydrous potassium carbonate, 70.9 g of 4-nitro-2-aminophenol and 500 ml of dry acetone. This procedure was repeated thrice. The reaction mixture was refluxed for 17 hours, then filtered. The solvent was evaporated from the filtrate under reduced pressure. The residue was washed with dilute sodium hydroxide solution, extracted with ether, then with methylene chloride. The solvent was evaporated separately from each extract. Thin layer chromatographic analysis indicated that the produce from each of the extracts was the same. The products was combined and recrystallized from ether to give 4, as a solid, m.p.: 88°–90° C.

EXAMPLE 5 ethyl 6-amino-3,4-dihydro-2H-1,4-benzoxazine-2-carboxylate hydrochloride (5)

Two 1-gram portions of 10% palladium-on-carbon catalyst were added to 10 g of 4 in 700 ml of ethanol. The mixture was hydrogenated at 50 p.s.i.g. for 2 hours. Fresh catalyst was added and the mixture was again hydrogenated. This procedure was repeated four times. Thin layer chromatographic analysis indicated that the nitro moiety had been completely converted to the amino moiety. The mixture was filtered and the filtrate was evaporated. Part of the resulting liquid, (5A), was dissolved in ethanol, then ether was added. The solution was cooled with an ice-bath and hydrogen chloride gas was bubbled into the solution until precipitation ceased. The precipitate was filtered, washed with ether and recrystallized from ethanol to give 5, as a solid, m.p.: 222° (with decomposition).

EXAMPLE 6 ethyl 3,4-dihydro-6-((methylsulfonyl)amino)-2H-1,4-benzoxazine-2-carboxylate (6)

A mixture of 14.7 g of 5A and 7.3 g of triethylamine in 200 ml of methylene chloride was treated with 8.3 g of methanesulfonyl chloride at 0°–5°. The mixture was then stirred for 2 hours, washed with water, dried, filtered, and the solvent was evaporated. The residue was mixed with 100 ml of ethanol and filtered. Recrystallization from ethanol gave 6 as a solid, m.p.: 149°–151°.

EXAMPLE 7 ethyl 6-(trifluoromethyl)-3,4-dihydro-2H-1,4-benzoxazine-2-carboxylate (7)

87.6 g of finely powdered sodium hydroxide was added in portions over an 8-hour period to a stirred solution of 164.0 g of 2-nitro-4-(trifluoromethyl)chlorobenzene in 200 ml of dimethyl sulfoxide at room temperature. The mixture was allowed to stand overnight, then poured into 1.5 liters of cold water. The resulting mixture was acidified to pH 1 with concentrated hydrochloric acid. An oil formed; it was separated and dissolved in ether. The solution was dried (MgSO$_4$) and stripped of solvent under reduced pressure. The residue was mixed with cold sodium hydroxide solution and the mixture was extracted with petroleum ether. The water layer was acidified with concentrated hydrochloric acid and the resulting oil was separated and dissolved in ether. The solution was dried (MgSO$_4$) and stripped of solvent to give 2-nitro-4-(trifluoromethyl)phenol (7A).

82.2 g of 7A was dissolved in 300 ml of ethanol. 0.5 g of platinum oxide catalyst was added and the mixture was hydrogenated at 50 p.s.i.g. Fresh portions of catalyst were added periodically. The resulting mixture was filtered, and the solvent was evaporated from the filtrate. The residue was crystallized from water to give 2-amino-4-trifluoromethyl-phenol (7B).

11.4 g of potassium carbonate was added to 48.7 g of 7B in 320 ml of acetone. Then 18.2 of ethyl 2,3-dibromopropionate was added dropwise to the refluxing mixture. This procedure was repeated thrice. The mixture was refluxed for 17 hours and filtered, and the filtrate was stripped of solvent under reduced pressure. The residue was dissolved in ether; the solution was washed with dilute sodium hydroxide solution, then dried (MgSO$_4$) and stripped of solvent. The residue was washed with petroleum ether and dried. The residue was mixed with ether and filtered. Part of the solvent was evaporated from the filtrate; the remaining solution was cooled. Crystals which formed were filtered and recrystallized from ether to give 7, m.p.: 105°–107°.

EXAMPLE 8 ethyl 6-methoxy-2,3-dihydro-2H-1,4-benzoxazine-2-carboxylate (8)

336.4 g of 2-nitro-4-methoxyaniline was refluxed for 20 hours with 200 g of sodium hydroxide and 10 g of arsenic trioxide, in 6500 ml of water. The resulting solution was cooled on an ice-bath, then acidified to pH 1 with concentrated hydrochloric acid. The solid which formed was filtered and washed with water and dried under reduced pressure over $P_2O_5$ to give 2-nitro-4-methoxyphenol, 8A, m.p.: 78°–80°.

193.1 g of 8A was mixed with 1400 ml of water and 513 ml of ammonium hydroxide was added. Then 595 g of powdered sodium dithionite was added in portions over a 50 minute period. The mixture then was stirred for 2 hours, the solid which formed was filtered and dried over $P_2O_5$ under reduced pressure to give 4-methoxy-2-aminophenol, 8B, m.p.: 134°136°.

A mixture of 56 g of 8B and 58.4 g of potassium carbonate in 640 ml of dry dimethylformamide was heated to 60° for 48 hours. The mixture then was poured into 4.5 liters of ice-water and extracted with ether. The extract was washed with water, then with 0.5 N sodium hydroxide solution, then was dried ($MgSO_4$) and the solvent evaporated under reduced pressure. The residue was wet column chromatographed over silica gel, eluents being ether/hexane (1.9 by volume), ether/hexane (1.4 by volume), ether/hexane (1:1 by volume). The last fraction obtained was dissolved in ether. The solution was chilled to give a solid, which was filtered and recrystallized from ether/petroleum ether (30°–60°) to give 1, as off-white crystals, m.p.: 59°–61°.

EXAMPLE 9 ethyl 6,7-dichloro-2,3-dihydro-2H-1,4-benzoxazine-2-carboxylate (9)

Over a period of two hours, sufficient concentrated nitric acid to provide 143.9 g of $HNO_3$ was added to a stirred solution of 48.5 g of 3,4-dichlorophenol in 360 ml of acetic acid, at 10°–20°. The resulting mixture was immediately poured onto ice. Solid product was collected, washed with water and suspended in ethanol. Filtration gave 3,4-dichloro-6-nitrophenol (9A), m.p.: 63°–65°.

106 g of 9A was suspended in 636 ml of water. 233 ml of ammonium hydroxide was added. 239.2 g of sodium dithionite was added over a period of about two hours at such a rate that the temperature of the reaction mixture was kept at about 50° C. The mixture was stirred at room temperature for two hours. The solid product was filtered, and extracted with methanol. Evaporation of the solvent from the extract gave 3,4-dichloro-6-aminophenol (9B).

9B was converted to 9 by the general procedure described in Example 4, 9 having a melting point of 88°–89°.

EXAMPLE 10 ethyl 7-methyl-3,4-dihydro-2H-1,4-benzoxazine-2-carboxylate (10)

m.p.: 90°–92° C., was prepared from 2-amino-5-methylphenol according to the procedure described in Example 2.

EXAMPLE 11 ethyl 8-chloro-6-nitro-3,4-dihydro-2H-1,4-benzoxazine-2-carboxylate (11)

m.p.: 141°–143°, was prepared from 2-chloro-4-nitro-6-aminophenol according to the procedure described in Example 3.

The precursor phenol was prepared as follows: 326.7 g of ammonium chloride and 52.5 ml of ammonium hydroxide were added to a stirred suspension of 187.6 g of 2-chloro-4,6-dinitrophenol in 1310 ml of water, at room temperature. The mixture was heated to 85°, 32.5 g of sodium sulfide was added and the mixture was stirred at 85° for 15 minutes. It then was filtered hot, the filtrate was cooled and filtered. The solid was dissolved in water. Acetic acid was added, the solid product was collected, and extracted with methanol. The solvent was evaporated to give the phenol.

EXAMPLE 12 ethyl 8-chloro-3,4-dihydro-2H-1,4-benzoxazine-2-carboxylate (12)

6-chloro-2-nitrophenol (12A) was prepared by treating 2-chlorophenol with nitric acid according to the procedure described for preparing 9A, in Example 9.

6-chloro-2-aminophenol (12B) was prepared from 12A according to the procedure described for preparing 9B in Example 9.

12, m.p.: 113°–114°, was prepared from 12B according to the procedure for preparing 4, described in Example 4.

EXAMPLE 13 ethyl 6-phenyl-3,4-dihydro-2H-1,4-benzoxazine-2-carboxylate (13)

m.p.: 141°–145°, was prepared from 4-phenyl-2-aminophenol according to the procedure described in Example 4.

EXAMPLE 14 ethyl 7-nitro-3,4-dihydro-2H-1,4-benzoxazine-2-carboxylate (14)

m.p.: 130°–132°, was prepared from 5-nitro-2-aminophenol according to procedures described in Example 4.

The esters of Formula I have been found to inhibit lipogenesis in tissues of mammals. The manner in which they cause this effect is not known with certainty; it is believed that they interfere with the synthesis of fatty acids in the tissue. Their effectiveness for this purpose has been ascertained by immersing samples of swine adipose tissue in a liquid medium containing radioactive glucose and the test chemical for a period of time, then isolating the lipid from the treated tissue and determining the up-take of the radioactive carbon by means of scintillation counting techniques. These tests were conducted in swine adipose tissue because in swine the primary site of lipogenesis—i.e., fatty acid synthesis—appears to be adipose tissue.

Described in more detail, the tests were conducted according to the following general procedure.

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 microCurie of glucose-U$^{14}$C, and 300 microunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound in each case. The data obtained from the tests were set out in Table I, as the percent inhibition of lipogenesis compared to the results obtained in the control tests wherein only the test compound was omitted.

TABLE I

| Compound No. | Percent Inhibition |
|---|---|
| 1A | 62 |
| 1 | 53 |
| 2 | 28 |
| 3 | 18 |
| 4 | 74 |
| 5 | 43 |
| 6 | 76 |
| 7 | 31 |
| 8 | 81 |
| 9 | 56 |
| 10 | 54 |
| 11 | 31 |
| 12 | 39 |
| 13 | 34 |
| 14 | 92 |

The esters of Formula I can be used to control lipogenesis in mammals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the esters orally or parenterally to the animal. They may be administered as such, or as an active ingredient of a conventional pharmaceutical formulation. They may be administered orally by any convenient means. Thus, they may be administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups, elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc, or vegetable gum can be used. The dosage of the ester needed to inhibit lipogenesis will depend upon the particular animal being treated. However, in general, satisfactory results are obtained when the esters are administered in a dosage of from about 1 to about 500 milligrams per kilogram of the animal's body weight. The ester can be administered in a single dose or a series of doses in the same day, or over a period of days. For any particular animal, a specific dosage regimen should be adjusted according to the individual need, the particular ester(s) used as the inhibitor, and the professional judgement of the person administering or supervising the administration of the inhibitor. It is to be understood that the dosages set forth herein are exemplary only, and that they do not, to any extent, limit the scope or practice of the invention.

I claim:

1. A method of inhibiting lipogenesis in a mammal, which comprises administering, to a mammal in need of such treatment, orally or parenterally an effective amount of a compound of the formula:

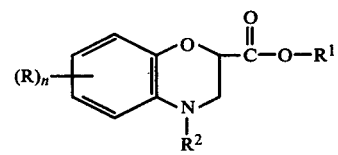

wherein n is zero, one or two, with the following provisos: (1) when n is one, r is middle halogen, nitro, amino, methylsulfonylamino, trifluoromethyl, phenyl, or alkyl or alkoxy of from one to six carbon atoms, bonded to a carbon atom in the 6-, 7-, or 8- position of the molecule; (2) when n is two, (a) R is nitro or middle halogen, bonded to carbon atoms in the 6- and 7- positions of the molecule; or is, 6-nitro, 8-chloro; R$^1$ is alkyl of from one to four carbon atoms, and R$^2$ is hydrogen or phenalkyl.

2. A method according to claim 1 wherein n is zero, R$^1$ is ethyl, and R$^2$ is hydrogen or benzyl.

3. A method according to claim 1 wherein n is 1, R is 6-nitro, 6-methoxy, 7-nitro, or 6-methylsulfonylamino, R$^1$ is ethyl and R$^2$ is hydrogen or benzyl.

4. A method according to claim 2 wherein R$^2$ is hydrogen.

5. A method according to claim 2 wherein R$^2$ is benzyl.

6. A method according to claim 3 wherein R is 6-nitro and R$^2$ is hydrogen.

7. A method according to claim 3 wherein R is 7-nitro and R$^2$ is hydrogen.

8. A method according to claim 3 wherein R is 6-methylsulfonylamino and R$^2$ is hydrogen.

9. A method according to claim 3 wherein R is 6-methoxy and R$^2$ is hydrogen.

* * * * *